(12) United States Patent
Chapman

(10) Patent No.: US 11,562,454 B2
(45) Date of Patent: Jan. 24, 2023

(54) HYBRID COLLIMATION TO LIMIT THE FIELD OF VIEW FOR GAMMA DETECTION PROBES AT HIGH AND LOW ENERGIES

(71) Applicant: Gregg J. Chapman, Plain City, OH (US)

(72) Inventor: Gregg J. Chapman, Plain City, OH (US)

(73) Assignee: Actis IP Holdings, LLC, Powell, OH (US)

( * ) Notice: Subject to any disclaimer, the term of this patent is extended or adjusted under 35 U.S.C. 154(b) by 0 days.

(21) Appl. No.: 17/148,724

(22) Filed: Jan. 14, 2021

(65) Prior Publication Data

US 2022/0082708 A1 Mar. 17, 2022

Related U.S. Application Data

(60) Provisional application No. 62/962,236, filed on Jan. 17, 2020.

(51) Int. Cl.
*G06Q 50/26* (2012.01)
*G06F 21/60* (2013.01)
(Continued)

(52) U.S. Cl.
CPC ......... *G06Q 50/265* (2013.01); *A61B 6/5294* (2013.01); *G01D 5/48* (2013.01); *G01T 1/1603* (2013.01); *G01T 1/202* (2013.01); *G01T 1/24* (2013.01); *G06F 9/54* (2013.01); *G06F 21/604* (2013.01); *G06F 21/62* (2013.01); *G06N 5/04* (2013.01); *G06N 20/00* (2019.01);
(Continued)

(58) Field of Classification Search
CPC ...... A61B 6/5294; G01D 5/48; G01T 1/1603; G01T 1/202; G01T 1/24; G06F 9/54; G06F 21/604; G06F 21/62; G06N 5/04; G06Q 50/01; G06Q 10/1093; G09B 19/00
See application file for complete search history.

(56) References Cited

U.S. PATENT DOCUMENTS 4,889,991 A * 12/1989 Ramsey ............... A61B 6/4258
250/363.01
6,144,876 A * 11/2000 Bouton ............... A61B 6/4258
600/436
(Continued)

*Primary Examiner* — David P Porta
*Assistant Examiner* — Fani Polyzos Boosalis
(74) *Attorney, Agent, or Firm* — Mueller Law, LLC; Jerry K. Mueller, Jr.

(57) ABSTRACT

A hybrid collimated probe incorporates two detectors consisting of a scintillating crystal or semiconductor material, such as Cadmium-Zinc-Telluride (CZT). The count rate measured on the rear detector is corrected for the shielding effect of the front detector before the count rate ratio is calculated. This is done by multiplying the rear detector count rate by a factor pre-determined from the thickness and density of the front detector for a specific radionuclide energy. The count rate ratio also must be corrected for the presence of background radiation at the target site. This is done by taking a 3 second average of the count rate over tissue that does not contain a radiotracer sequestered at the site of pathology, but in adjacent tissue that is uniformly perfused by a lower level concentration of the radiotracer circulating in the blood pool background.

19 Claims, 3 Drawing Sheets

(51) Int. Cl.
*G06F 21/62* (2013.01)
*G06F 9/54* (2006.01)
*G06Q 50/00* (2012.01)
*G06N 5/04* (2006.01)
*G09B 19/00* (2006.01)
*G06N 20/00* (2019.01)
*A61B 6/00* (2006.01)
*G01D 5/48* (2006.01)
*G01T 1/16* (2006.01)
*G01T 1/202* (2006.01)
*G01T 1/24* (2006.01)
*H04L 67/53* (2022.01)
*H04L 67/50* (2022.01)
*G06Q 10/10* (2012.01)

(52) U.S. Cl.
CPC ............. *G06Q 50/01* (2013.01); *G09B 19/00* (2013.01); *H04L 67/53* (2022.05); *H04L 67/535* (2022.05); *G06Q 10/1093* (2013.01)

(56) References Cited

U.S. PATENT DOCUMENTS

| | | | |
|---|---|---|---|
| 6,236,880 B1* | 5/2001 | Raylman | ............... G01T 1/161 600/436 |
| 2004/0037394 A1* | 2/2004 | Kuroda | ............... G01T 1/2907 378/205 |

* cited by examiner

HYBRID COLLIMATION TO LIMIT THE FIELD OF VIEW FOR GAMMA DETECTION PROBES AT HIGH AND LOW ENERGIES

CROSS-REFERENCE TO RELATED APPLICATIONS

This application claims benefit of provisional 62/962,236 filed Jan. 17, 2020, and is cross-referenced to commonly owned U.S. Ser. No. 17/148,705, filed Jan. 14, 2021, provisional 62/962,232 filed Jan. 17, entitled "A Compensated Dual Element Detector for Measuring the Distance to a Radio-Labeled Source") and U.S. Ser. No. 17/148,716, filed Jan. 14, 2021, provisional 62/962,234 filed January 17, entitled "Electronic Collimation and Depth Detection in a Side-Viewing Laparoscopic Probe for the Detection of High Energy Gamma Radiation").

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM

Not applicable.

STATEMENT REGARDING PRIOR DISCLOSURES BY THE INVENTOR OR A JOINT INVENTOR

Not applicable.

BACKGROUND OF THE INVENTION

Intraoperative detection of radiolabeled tissue has become a common practice in surgical oncology. Recent improvements in surgical technique have led to laparoscopic and robotic surgical approaches as opposed to open exposure of the surgical site, particularly in OB/GYN, urological, and abdominal procedures. Gamma detection probes that can be passed through a standard 12-millimeter port (Trocar™) are commercially available for the detection of radionuclides with low energy emissions (less than 300 KeV). In order to detect high energy gamma emission, such as the annihilation from residual positron emitting radioisotopes (511 KeV), heavy metal shielding of 9 mm thickness (radially) or greater is required. It is not possible to produce a probe capable of being passed through a 12 mm surgical port using this form of shielding.

Electronic collimation using two co-axial detectors can be used to eliminate the need for thick metal shielding at high energies. The dual detector probe can limit the field of view by inhibiting counting at the system level whenever the source is outside of the volume specified by a predefined threshold value for the count rate ratio of the two detectors. The Inverse Squared Law is applied to estimate the distance to the gamma source and the extent of the field of view. This method of limiting the field of view and distance estimation has been previously described and incorporated in Chapman, G. J. (2017). *"High Energy Gamma Detection for Minimally Invasive Surgery"*, (Doctoral dissertation), The Ohio State University, Columbus, Ohio, ProQuest Dissertations Publishing, 2017, 27539296.

The co-axial alignment of the two probe detectors introduces loss of gamma counts in the rear detector due to the shielding effect of the front detector material. Since the geometry and material of the front detector are known, the count rate of the rear detector can be multiplied by a correction factor to estimate the unshielded count rate, as described in U.S. Ser. No. 17/148,705, filed Jan. 14, 2021 (U.S. Provisional 62/962,232 filed Jan. 17, 2020. At lower gamma energies the count loss due to the shielding effect is greater than the number of counts detected on the rear detector (loss is >50%), resulting in a correction factor greater than 2.00 and grows without bound at lower energies. For this reason, electronic collimation using a CZT detector material is limited to gamma energies greater than 234 KeV.

For gamma energies of 234 KeV or less, heavy metal shielding is still a viable option to implement probes of 12 mm diameter. If tungsten shielding is used, a thickness of 1.53 mm is sufficient to block 80% of gamma emissions at 234 KeV. Lower energies would be attenuated to a greater extent.

By including sufficient shielding to collimate the gamma detection probe at less than 234 KeV and including a second detector to provide electronic collimation for energies greater than 234 KeV, a hybrid collimation solution can be realized in a 12 mm diameter probe design.

Whenever metallic collimation is used, the front detector must be recessed in the shielding to limit the field of view for the probe to a specific angle. This reduces the sensitivity of the probe since the distance to the source is increased by the depth of the collimator. For a 5 mm diameter detector, 5 mm of collimation is required to limit the field of view to 90 degrees (see FIG. 1). Although this represents a significant reduction in sensitivity, this recessed distance is equivalent to the near field of the detector, and the Inverse Squared Law cannot be applied for accurate electronic collimation. Similarly, depth detection is limited to radionuclides with emissions greater than 234 KeV.

BRIEF SUMMARY OF INVENTION

By including sufficient shielding to collimate the gamma detection probe at less than 234 KeV and including a second detector to provide electronic collimation for energies greater than 234 KeV, a hybrid collimation solution can be realized in a 12 mm diameter probe design. It is essential that the count rate measured on the rear detector is corrected for the shielding effect of the front detector before the count rate ratio is calculated. The count rate ratio also must be corrected for the presence of background radiation at the target site. The measured background count is subtracted from both the front and rear detector counts, as it is assumed to be uniform in the direction of the probe and, unlike the target emission, can be assumed to be a parallel flux field that is constant over small differences in distance.

BRIEF DESCRIPTION OF THE SEVERAL VIEWS OF THE DRAWINGS

For a fuller understanding of the nature and advantages of the present method and process, reference should be had to the following detailed description taken in connection with the accompanying drawings, in which.

These drawings will be described in more detail below.

DETAILED DESCRIPTION OF THE INVENTION

Figure 1:
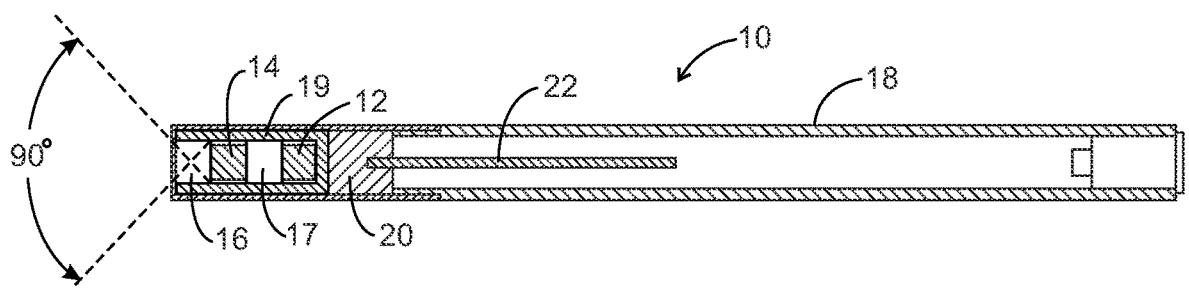
FIG. 1 illustrates a dual detector probe capable of electronic collimation and collimation using heavy metal for low energy radionuclides.
Figure 1A:
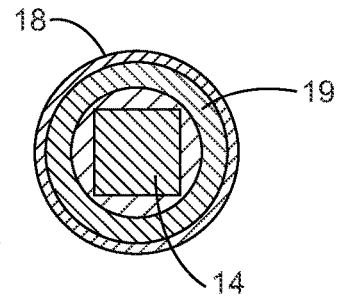
FIG. 1A is an end view looking into the forward end of the probe.

In the end viewing configuration as illustrated in FIG. 1, a hybrid collimated probe, 10, incorporates two detectors, 12 and 14, consisting of a scintillating crystal or semiconductor material, such as Cadmium-Zinc-Telluride (CZT). Semiconductor crystals are energized with a bias voltage (60-240 Volts) on alternating anodes and grounded on alternating cathodes, with the cathode located on the distal aspect of each crystal to form a charge collecting detector. Charge integration and pulse shaping are provided by a pre-amplifier circuit incorporated in the handle of the probe. A Teflon® or other low gamma absorbing spacer, 16, in used to recess the front detector in tungsten shielding, 19, for collimation at energies less than 234 KeV (for CZT). See also FIG. 1A. All probe materials are enclosed within medical grade 316 stainless steel or aluminum annular housing, 18. Also shown is a pre-amplifier bracket, 20, and pre-amplifier(s), 22. Detectors 12 and 14 are separated by an insulated (low gamma absorbing) spacer, 17, such as Teflon®.

The signal from the dual detector probe consists of two channels of charge pulses. The pre-amplifier is gain trimmed to provide 6 mV/KeV amplitude pulses. Forward crystal 14 acts as the primary count rate detector. Rear crystal 12 is used to measure the count rate ratio of the two detectors separated by a fixed distance. The count rate ratio can be used to calculate the distance to the radiation source, and provide electronic collimation based on the Inverse Squared Law.

It is essential that the count rate measured on the rear detector is corrected for the shielding effect of the front detector before the count rate ratio is calculated. This is done by multiplying the rear detector count rate by a factor pre-determined from the thickness and density of the front detector for a specific radionuclide energy. The radionuclide is selected on the gamma detection system console and the correction factor is loaded from a database incorporated in the console.

The count rate ratio also must be corrected for the presence of background radiation at the target site. This is done by taking a 3 second average of the count rate over tissue that does not contain a radiotracer sequestered at the site of pathology, but in adjacent tissue that is uniformly perfused by a lower level concentration of the radiotracer circulating in the blood pool background. The measured background count is subtracted from both the front and rear detector counts as it is assumed to be uniform in the direction of the probe and, unlike the target emission, can be assumed to be a parallel flux field that is constant over small differences in distance.

Once the rear count rate is corrected for the shielding effect of the front detector and both detectors are corrected for the measured background count, the ratio of the front count rate divided by the rear count rate is compared to a threshold value that defines the extent of the field of view mathematically in the probe control unit. The extent of the field is calculated as:

$$\text{FOV Limit} = \frac{x * (\cos\varphi + \sqrt{\cos^2\varphi + R_{THRESHOLD} - 1})}{(R_{THRESHOLD} - 1)}$$

where, x is the fixed distance between the two detectors;

φ is the off axis angle in the direction of the source; and $R_{THRESHOLD}$ is the value that the count rate ratio must exceed to enable counting.

Figure 2:
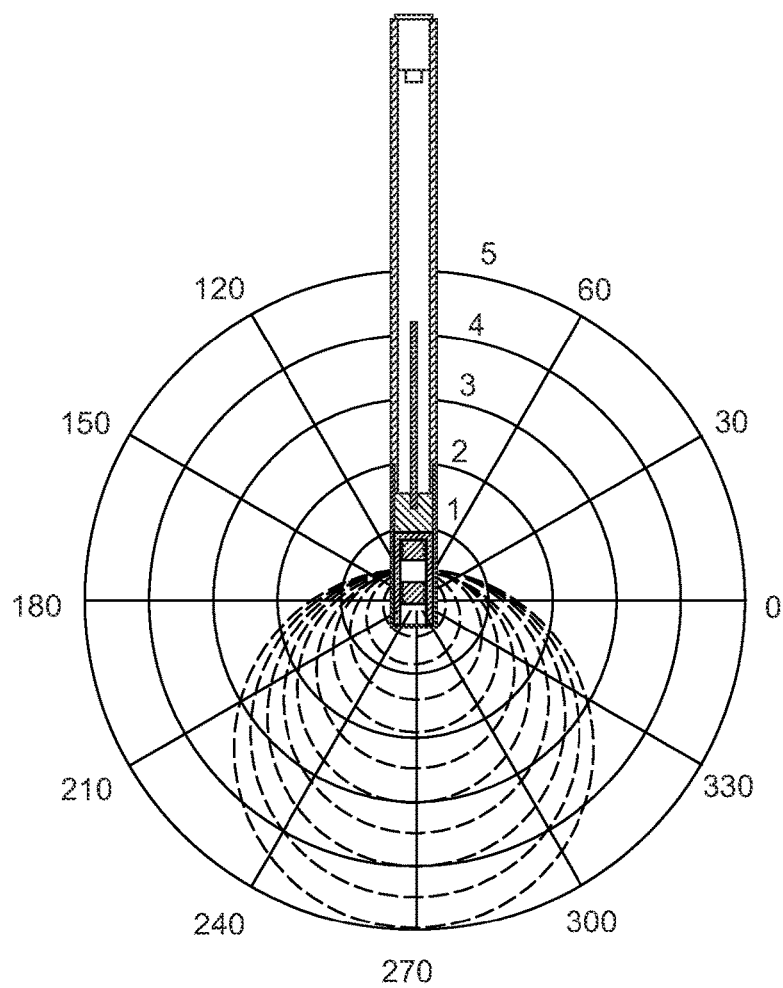
FIG. 2 illustrates the various contours for the electronically collimated field of view at different values of $R_{THRESHOLD}$. The CZT is recessed within the tungsten shielding to provide hybrid collimation at low energies.

FIG. 2 illustrates the electronically collimated field of view for various values of $R_{THRESHOLD}$.

The distance to the radioactive source is estimated as:

$$\text{depth} = \frac{x}{\sqrt{\frac{(N_F - N_B)}{((N_R - N_B) * K_{SHIELDING})} - 1}}$$

where, $$K_{SHIELDING} = \frac{1}{(1 - e^{-\mu_l T})};$$

$\mu_l$ is the linear attenuation coefficient for the detector material and the energy of the gamma emission; and T is the thickness of the front detector material.

The lower end of the energy range for the algorithm is limited to the value to prevent $K_{SHIELDING}$ from exceeding 2.00.

FIG. 2 illustrates the various contours for the electronically collimated field of view at different values of $R_{THRESHOLD}$. The CZT is recessed within the tungsten shielding to provide hybrid collimation at low energies.

Figure 3:
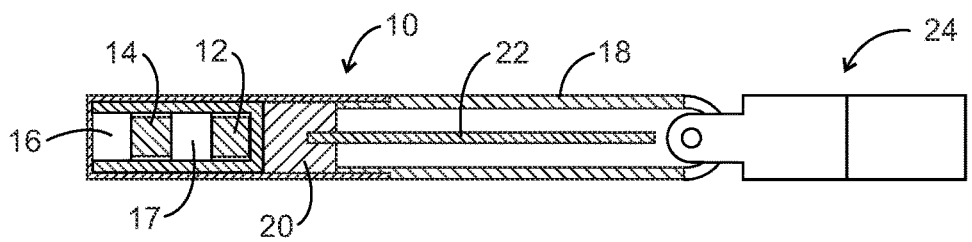
FIG. 3 illustrates an end-viewing dual detector probe capable of electronic collimation can be placed on an da Vinci® Endowrist® system to provide angulation of the field of view within the surgical cavitation.
Figure 4:
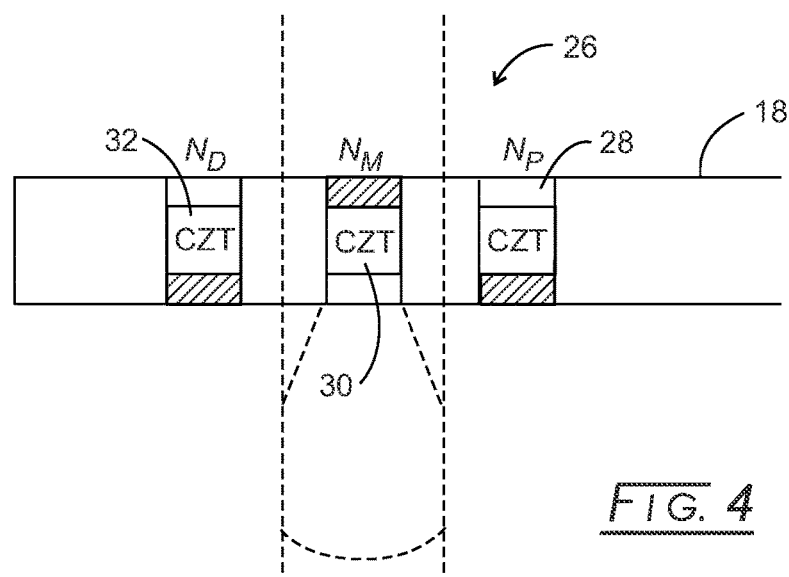
FIG. 4 illustrates a side-viewing probe intended for laparoscopic use. Three detectors are required. Heavy metal shielding is used to increase or decrease the count rate ratio for electronic collimation.
Figure 4A:
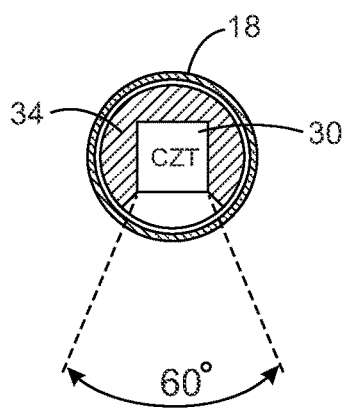
FIG. 4A is an end view of the laparoscopic probe.
Figure 4B:
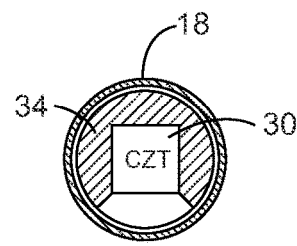
FIG. 4B is a sectional view through the middle detector of the new laparoscopic probe.
Figure 4C:
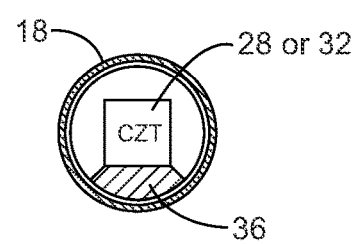
FIG. 4C is a sectional view through the flanking detectors.

Other configurations using three or more detectors and a combination of metallic and electronic collimation also are possible. Since the outside diameter of the end-viewing probe is 12 mm, it can be introduced into the surgical field through a standard Trocar™ for laparoscopic and robotic approaches. In these applications, the dual detection element and associated electronics can be mounted at the distal end of an articulated probe for robotic surgery as an alternative to a side-viewing probe (FIG. 3). In particular, probe 10 is seen mounted to the end of a robotic arm, 24, such as a da Vinci® Endowrist® system.

A side viewing probe for laparoscopy can be implemented using three detectors and hybrid collimation as well, as disclosed in U.S. Ser. No. 62/962,234 filed Jan. 17, 2020 (see FIGS. 4, 4A, 4B, and 4C). In particular, a laparoscopic probe, 26, uses 3 detector crystals, 28, 30, and 32, configured for lateral view for counting pulses from a gamma radiation source, where measured counts, respectively, are $N_P$, $N_M$, and $N_D$. With tungsten shielding, 34, for central crystal 30 configured for a 60° field of view and flanking crystals 28 and 32 having tungsten shielding, 36. Since the count rate of the middle detector is attenuated outside of the angular field of view, the count rate ratios of the following equation are similarly reduced by 32%, forcing the count rate ratios to a value less than unity. Outside of the 60° arc, the count rate ratios are less than 1, and counting is inhibited by the probe control unit.

$$\frac{N_M}{N_D} \text{ or } \frac{N_M}{N_P} = 0.68 \frac{N_M}{N_{either}} \text{ outside the } FOV$$

Figure 5:
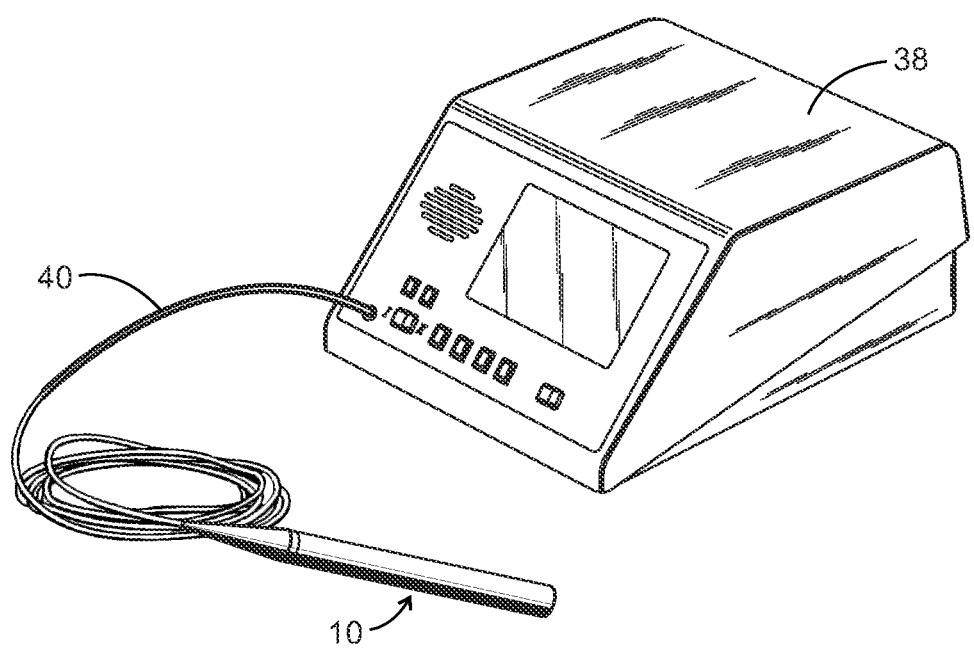
FIG. 5 illustrates a gamma detection control unit and hand-held probe.

Probes can interface to a Gamma Detection System console, 38, shown in FIG. 5 using a multiconductor cable and connectors, 40, or wireless standard modules such as Bluetooth™, can be incorporated in the design to obviate the need for a cable with a sufficient number of conductors for two or more channels of gamma radiation pulses (FIG. 5).

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

The invention claimed is:

1. A hand-held probe for detecting a source of radiation, which comprises:
   (a) an elongate annular housing having a forward end and a rear end, and being devoid of side shielding;
   (b) a pair of co-axial radiation detecting elements, a forward co-axial radiation detecting element and a rear co-axial radiation detecting element, the co-axial radiation detecting elements separated by a material of low gamma absorption, the forward co-axial radiation detecting element located at the annular housing forward end and not being recessed, the pair of co-axial radiation detecting elements including sufficient shielding to collimate the hand-held probe at less than 234 KeV sources of radiation;
   (c) one or more preamplifiers located adjacent and rearward of the pair of co-axial radiation detecting elements and in electrical connection therewith;
   (d) a console in communication with the pair of co-axial radiation detecting elements and housing a software algorithm to determine the distance, d, to a radiation source, according to the following equation:

$$d = \frac{x}{\left(\sqrt{\frac{N_F}{N_R}} - 1\right)}$$

where,
   $N_F$ is the number of gamma counts received by the forward co-axial radiation detecting element;
   $N_R$ is the number of gamma counts received by the rear co-axial radiation detecting element;
   x is the fixed distance between the two detectors; and
   d is the distance from the gamma emission source to the detector.

2. The hand-held probe of claim 1, wherein the software algorithm corrects count rates for both co-axial radiation detecting elements by subtracting background radiation count, $N_B$, from both $N_F$ and $N_R$ before determining the distance d.

3. The hand-held probe of claim 2, wherein lower end of the energy range for the software algorithm is limited to the value to prevent $K_{SHIELDING}$ from exceeding 2.00.

4. The hand-held probe of claim 3, wherein the software algorithm calculates the corrected distance to a radiation source, according to the following equations:

$$\text{depth} = \frac{x}{\sqrt{\frac{(N_F - N_B)}{((N_R - N_B) * K_{SHIELDING})} - 1}}$$

where, $$K_{SHIELDING} = \frac{1}{(1 - e^{-\mu_l T})};$$

$\mu_l$ is the linear attenuation coefficient for the detector material and the energy of the gamma emission; and
T is the thickness of the forward co-axial radiation detecting element.

5. The hand-held probe of claim 4, wherein the software algorithm further limits the field of view by inhibiting counting whenever the radiation source is outside of the volume specified by a threshold value for count rate ratio, $R_{THRESHOLD}$ according to the following equation:

$$FOV \text{ Limit} = \frac{x * \left(\cos\varphi + \sqrt{\cos^2\varphi + R_{THRESHOLD} - 1}\right)}{(R_{THRESHOLD} - 1)}$$

where:
   x is the fixed distance between the pair of co-axial radiation detecting elements;
   $\phi$ is the off-axis angle in the direction of the source; and
   $R_{THRESHOLD}$ is the value that the count rate ratio must exceed to enable counting.

6. The hand-held probe of claim 5, which is calibrated for each specific source of radiation at or above about 511 KeV to provide a correction factor for the shielding effect of the forward co-axial radiation detecting element on the rear co-axial radiation detecting element.

7. The hand-held probe of claim 1, wherein the pair of co-axial radiation detecting elements comprise one or more of a semiconductor, a diode, or a scintillation element.

8. The hand-held probe of claim 1, wherein the diameter of the elongate annular housing is less than about 12 millimeters.

9. The hand-held probe of claim 1, wherein the communication of the console with the pair of co-axial radiation detecting elements is electrical communication.

10. The hand-held probe of claim 1, wherein the communication of the console with the pair of co-axial radiation detecting elements is wireless communication.

11. The hand-held probe of claim 1, wherein the communication of the console with the pair of co-axial radiation detecting elements is electrical communication or wireless communication.

12. A hand-held probe for detecting a source of radiation, which comprises:
(a) an elongate annular housing having a forward end and a rear end, and being devoid of side shielding;
(b) a pair of co-axial radiation detecting elements, a forward co-axial radiation detecting element and a rear co-axial radiation detecting element, the co-axial radiation detecting elements separated by a material of low gamma absorption, the forward co-axial radiation detecting element located at the annular housing forward end and not being recessed, the pair of co-axial radiation detecting elements including sufficient shielding to collimate the hand-held probe at less than 234 KeV sources of radiation;
(c) one or more preamplifiers located adjacent and rearward of the pair of co-axial radiation detecting elements and in electrical connection therewith;
(d) a console in communication with the pair of co-axial radiation detecting elements and housing a software algorithm to determine the distance, d, to a radiation source, according to the following equation:

$$d = \frac{x}{\left(\sqrt{\frac{N_F}{N_R}} - 1\right)}$$

where,
$N_F$ is the number of gamma counts received by the forward co-axial radiation detecting element;
$N_R$ is the number of gamma counts received by the rear co-axial radiation detecting element;
x is the fixed distance between the two detectors; and
d is the distance from the gamma emission source to the detector,
wherein the software algorithm compensates for shielding by multiplying rear radiation detecting element count rate by the $K_{SHIELDING}$ factor resulting in the software algorithm for a corrected distance, as follows:

$$depth = \frac{x}{\sqrt{\frac{(N_F - N_B)}{((N_R - N_B) * K_{SHIELDING})} - 1}}$$

where, $$K_{SHIELDING} = \frac{1}{(1 - e^{-\mu_l T})};$$

$\mu_l$ is the linear attenuation coefficient for the material of the pair of co-axial radiation detecting elements and the energy of the gamma emission; and T is the thickness of the forward co-axial radiation detecting element.

13. The hand-held probe of claim 12, wherein the software algorithm also corrects count rates for both co-axial radiation detecting elements by subtracting background radiation count, $N_R$, from both $N_F$ and $N_R$ before determining the distance d.

14. The hand-held probe of claim 13, wherein a lower end of the energy range for the software algorithm is limited to the value to prevent $K_{SHIELDING}$ from exceeding 2.00.

15. The hand-held probe of claim 14, wherein the software algorithm calculates the corrected distance to a radiation source, according to the following equations:

$$depth = \frac{x}{\sqrt{\frac{(N_F - N_B)}{((N_R - N_B) * K_{SHIELDING})} - 1}}$$

where, $$K_{SHIELDING} = \left(\frac{1}{(1 - e^{-\mu_l T})}\right)$$

$\mu_l$ is the linear attenuation coefficient for the detector material and the energy of the gamma emission; and
T is the thickness of the forward co-axial radiation detecting element.

16. The hand-held probe of claim 15, wherein the software algorithm further limits the field of view by inhibiting counting whenever the radiation source is outside of the volume specified by a threshold value for count rate ratio, $R_{THRESHOLD}$ according to the following equation:

$$FOV\ Limit = \frac{x * \left(\cos\varphi + \sqrt{\cos^2\varphi + R_{THRESHOLD} - 1}\right)}{(R_{THRESHOLD} - 1)}$$

where:
x is the fixed distance between the pair of co-axial radiation detecting elements;
φ is the off-axis angle in the direction of the source; and
$R_{THRESHOLD}$ is the value that the count rate ratio must exceed to enable counting.

17. The hand-held probe of claim 16, which is calibrated for each specific source of radiation at or above about 511 KeV to provide a correction factor for the shielding effect of the forward co-axial radiation detecting element on the rear co-axial radiation detecting element.

18. The hand-held probe of claim 12, wherein the pair of co-axial radiation detecting elements comprise one or more of a semiconductor, a diode, or a scintillation element.

19. The hand-held probe of claim 12, wherein the diameter of the elongate annular housing is less than about 12 millimeters.

\* \* \* \* \*